US005593959A

United States Patent [19]

Miller et al.

[11] Patent Number: 5,593,959

[45] Date of Patent: Jan. 14, 1997

[54] MUTATIONS IN THE GENE ENCODING THE ALPHA CHAIN OF PLATELET GLYCOPROTEIN IB

[75] Inventors: Jonathan L. Miller; David Cunningham; Vicki A. Lyle, all of Syracuse; Clara N. Finch, Webster; Matthew R. Pincus, Syracuse, all of N.Y.

[73] Assignee: The Research Foundation of State University of New York, Albany, N.Y.

[21] Appl. No.: 135,929

[22] Filed: Oct. 14, 1993

Related U.S. Application Data

[62] Division of Ser. No. 770,968, Oct. 7, 1991, Pat. No. 5,317,097.

[51] Int. Cl.[6] ...................... C07K 14/705; C07K 14/745; A61K 38/17; A61K 38/36

[52] U.S. Cl. .............................. 514/8; 530/380; 530/395; 424/94.63; 424/94.64; 128/899

[58] Field of Search .................................... 530/380, 395; 424/94.63, 94.64; 514/8; 128/899

[56] References Cited

FOREIGN PATENT DOCUMENTS 9109614 7/1991 WIPO .

OTHER PUBLICATIONS

J. L. Miller et al. "Patients with Platelet-type von Willebrand . . . " Circulation 82(4 Suppl. 3) III 595 (1990).

J. L. Miller et al. "Mutation in the Gene Encoding the α-chain . . . " Proc. Natl. Acad. Sci. 88:4761–4765 (Jun. 1991).

R. I. Handin et al. Blood. 74:129a (1989).

A. Wicki et al. "The Glycoprotein Ib Complex of Human Blood Platelets" Eur. J. Biochem 163:43–50 (1987).

V. A. Canfield et al. "Isolation and Characterization of the α and β. . . " Biochem. Biophys. Res. Commun. 147(2)526–534 (Sep. 1987).

J. L. Miller et al. "von Willebrand Factor Binds to Platelets . . . " J. Clin. Invest. 72:1532–1542 (Nov. 1983).

J. N. George et al. "Molecular Defects in Interactions of Platelets . . . " New. Engl. J. Med. 311(17)1084–1098 (Oct. 1984).

S. D. Russell and G. J. Roth, Blood 81: 1787–1791 (1993).

Max Vasquez, et al., "Helix–Coil Transition Theory Including Long–Range Electrostatic Interactions: Application to Globular Proteins", Biopolymers 26: 351–371 (1987).

James M. Chen, et al., "Conformations of the central transforming region (Ile 55–Met 67) of the p21 protein and their relationship to activation of the protein", Int. J. Peptide Res. 36; 247–254 (1990).

James Chen, et al., "Comparative X–ray Crystallographic Evidence for a β–Bend Conformation as the Active Structure for Peptide T in T4 Receptor Recognition", Journal of Protein Chemistry, 8: 87–100 (1989).

Matthew R. Pincus, "The Chain Build–Up Procedure in Computing the Structures of Biologically Active Polypeptides and Proteins", International Journal of Quantum Chemistry: Quantum Biology Symposium, 15: 209–220 (1988).

Dipak Shah, et al., "Correlation of β–bend conformations of tetrapeptides with their activities in CD4–receptor binding assays", Int. J. Peptide Protein Res. 34: 325–332 (1989).

James M. Chen, et al., "Comparison of the Predicted Structure for the Activated Form of the P21 Protein with the X–ray Crystal Structure", Journal of Protein Chemistry 9: 543–547 (1990).

*Primary Examiner*—Charles L. Patterson, Jr.
*Assistant Examiner*—Rebecca Prouty
*Attorney, Agent, or Firm*—Nixon, Hargrave, Devans & Doyle

[57] ABSTRACT

The subject invention provides purified polypeptides encoded by naturally-occurring wild-type platelet glycoprotein Ib alpha having a mutation which renders the polypeptide more reactive with von Willebrand factor. Preferably, the mutation is in the hinge region of GP Ibα, such as the substitution of valine for glycine at residue 233. These mutations alter the three-dimensional structure of the mutant polypeptide from a beta bend conformation to an alpha helix formation, and also create an amphipathic region within the mutant polypeptide. DNA encoding the mutant polypeptides, as well as expression systems for the production of the mutant polypeptides, are also provided. Methods and compositions using the mutant polypeptides and DNA oligomers complementary to the mutant polypeptides are further provided.

17 Claims, 2 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 31 base pairs
( B ) TYPE: nucleic acid -continued ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

TACTGAATTC CTCATGCCTC TCCTCCTCTT G 31

( 2 ) INFORMATION FOR SEQ ID NO:2:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

TTGTCCTGCA GCCAGCGACG AAAATAGAGG A 31

( 2 ) INFORMATION FOR SEQ ID NO:3:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

TTCGTCGCTG GCTGCAG 17

( 2 ) INFORMATION FOR SEQ ID NO:4:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

GGCTGTCTAG AGAAGCA 17

( 2 ) INFORMATION FOR SEQ ID NO:5:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

AAGCAAGGTG TGGACG 16

( 2 ) INFORMATION FOR SEQ ID NO:6:

( i ) SEQUENCE CHARACTERISTICS:
( A ) LENGTH: 16 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

AAGCAAGTTG TGGACG 16

( 2 ) INFORMATION FOR SEQ ID NO:7:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:7:

CTGCAGGACA ATGCTGAAAA TGTCTACGTA 30

( 2 ) INFORMATION FOR SEQ ID NO:8:

( i ) SEQUENCE CHARACTERISTICS:
( A ) LENGTH: 30 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:8:

CCGGATCCCA ACTAGATTCC AATAGGAGAG 30

( 2 ) INFORMATION FOR SEQ ID NO:9:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:9:

Tyr Val Trp Lys Gln Gly Val Asp Val Lys Ala
1 5 10

-continued ( 2 ) INFORMATION FOR SEQ ID NO:10:

( i ) SEQUENCE CHARACTERISTICS:
( A ) LENGTH: 11 amino acids
( B ) TYPE: amino acid
( D ) TOPOLOGY: linear ( i i ) MOLECULE TYPE: peptide ( x i ) SEQUENCE DESCRIPTION: SEQ ID NO:10:

| | | | | | | | | | | |
|---|---|---|---|---|---|---|---|---|---|---|
| Tyr | Val | Trp | Lys | Gln | Val | Val | Asp | Val | Lys | Ala |
| 1 | | | | 5 | | | | | 10 | |

( 2 ) INFORMATION FOR SEQ ID NO:11:

( i ) SEQUENCE CHARACTERISTICS:
( A ) LENGTH: 610 amino acids
( B ) TYPE: amino acid
( D ) TOPOLOGY: linear ( i i ) MOLECULE TYPE: protein ( x i ) SEQUENCE DESCRIPTION: SEQ ID NO:11:

| | | | | | | | | | | | | | | | |
|---|---|---|---|---|---|---|---|---|---|---|---|---|---|---|---|
| His | Pro | Ile | Cys | Glu | Val | Ser | Lys | Val | Ala | Ser | His | Leu | Glu | Val | Asn |
| 1 | | | | 5 | | | | | 10 | | | | | 15 | |
| Cys | Asp | Lys | Arg | Asn | Leu | Thr | Ala | Leu | Pro | Pro | Asp | Leu | Pro | Lys | Asp |
| | | | 20 | | | | | 25 | | | | | 30 | | |
| Thr | Thr | Ile | Leu | His | Leu | Ser | Glu | Asn | Leu | Leu | Tyr | Thr | Phe | Ser | Leu |
| | | 35 | | | | | 40 | | | | | 45 | | | |
| Ala | Thr | Leu | Met | Pro | Tyr | Thr | Arg | Leu | Thr | Gln | Leu | Asn | Leu | Asp | Arg |
| | 50 | | | | | 55 | | | | | 60 | | | | |
| Cys | Glu | Leu | Thr | Lys | Leu | Gln | Val | Asp | Gly | Thr | Leu | Pro | Val | Leu | Gly |
| 65 | | | | | 70 | | | | | 75 | | | | | 80 |
| Thr | Leu | Asp | Leu | Ser | His | Asn | Gln | Leu | Gln | Ser | Leu | Pro | Leu | Leu | Gly |
| | | | | 85 | | | | | 90 | | | | | 95 | |
| Gln | Thr | Leu | Pro | Ala | Leu | Thr | Val | Leu | Asp | Val | Ser | Phe | Asn | Arg | Leu |
| | | | 100 | | | | | 105 | | | | | 110 | | |
| Thr | Ser | Leu | Pro | Leu | Gly | Ala | Leu | Arg | Gly | Leu | Gly | Glu | Leu | Gln | Glu |
| | | 115 | | | | | 120 | | | | | 125 | | | |
| Leu | Tyr | Leu | Lys | Val | Asn | Glu | Leu | Lys | Thr | Leu | Pro | Pro | Gly | Leu | Leu |
| | 130 | | | | | 135 | | | | | 140 | | | | |
| Thr | Pro | Thr | Pro | Lys | Leu | Glu | Lys | Leu | Ser | Leu | Ala | Asn | Asn | Asn | Leu |
| 145 | | | | | 150 | | | | | 155 | | | | | 160 |
| Thr | Glu | Leu | Pro | Val | Gly | Leu | Leu | Asn | Gly | Leu | Glu | Asn | Leu | Asp | Thr |
| | | | | 165 | | | | | 170 | | | | | 175 | |
| Leu | Leu | Leu | Gln | Glu | Asn | Ser | Leu | Tyr | Thr | Ile | Pro | Lys | Gly | Phe | Phe |
| | | | 180 | | | | | 185 | | | | | 190 | | |
| Gly | Ser | His | Leu | Leu | Pro | Phe | Ala | Phe | Leu | His | Gly | Asn | Pro | Trp | Leu |
| | | 195 | | | | | 200 | | | | | 205 | | | |
| Cys | Asn | Cys | Glu | Ile | Leu | Tyr | Phe | Arg | Arg | Trp | Leu | Gln | Asp | Asn | Ala |
| | 210 | | | | | 215 | | | | | 220 | | | | |
| Glu | Asn | Val | Tyr | Val | Trp | Lys | Gln | Gly | Val | Asp | Val | Lys | Ala | Met | Thr |
| 225 | | | | | 230 | | | | | 235 | | | | | 240 |
| Ser | Asn | Val | Ala | Ser | Val | Gln | Cys | Asp | Asn | Ser | Asp | Lys | Phe | Pro | Val |
| | | | | 245 | | | | | 250 | | | | | 255 | |
| Tyr | Lys | Tyr | Pro | Gly | Lys | Gly | Cys | Pro | Thr | Leu | Gly | Asp | Glu | Gly | Asp |
| | | | 260 | | | | | 265 | | | | | 270 | | |
| Thr | Asp | Leu | Tyr | Asp | Tyr | Tyr | Pro | Glu | Glu | Asp | Thr | Glu | Gly | Asp | Lys |

-continued

| | | | | | | | | | | | | | | | |
|---|---|---|---|---|---|---|---|---|---|---|---|---|---|---|---|
| | | 275 | | | | | 280 | | | | | 285 | | | |
| Val | Arg | Ala | Thr | Arg | Thr | Val | Val | Lys | Phe | Pro | Thr | Lys | Ala | His | Thr |
| | 290 | | | | | 295 | | | | | 300 | | | | |
| Thr | Pro | Trp | Gly | Leu | Phe | Tyr | Ser | Trp | Ser | Thr | Ala | Ser | Leu | Asp | Ser |
| 305 | | | | | 310 | | | | | 315 | | | | | 320 |
| Gln | Met | Pro | Ser | Ser | Leu | His | Pro | Thr | Gln | Glu | Ser | Thr | Lys | Glu | Gln |
| | | | | 325 | | | | | 330 | | | | | 335 | |
| Thr | Thr | Phe | Pro | Pro | Arg | Trp | Thr | Pro | Asn | Phe | Thr | Leu | His | Met | Glu |
| | | | 340 | | | | | 345 | | | | | 350 | | |
| Ser | Ile | Thr | Phe | Ser | Lys | Thr | Pro | Lys | Ser | Thr | Thr | Glu | Pro | Thr | Pro |
| | | 355 | | | | | 360 | | | | | 365 | | | |
| Ser | Pro | Thr | Thr | Ser | Glu | Pro | Val | Pro | Glu | Pro | Ala | Pro | Asn | Met | Thr |
| | 370 | | | | | 375 | | | | | 380 | | | | |
| Thr | Leu | Glu | Pro | Thr | Pro | Ser | Pro | Thr | Thr | Pro | Glu | Pro | Thr | Ser | Glu |
| 385 | | | | | 390 | | | | | 395 | | | | | 400 |
| Pro | Ala | Pro | Ser | Pro | Thr | Thr | Pro | Glu | Pro | Thr | Pro | Ile | Pro | Thr | Ile |
| | | | | 405 | | | | | 410 | | | | | 415 | |
| Ala | Thr | Ser | Pro | Thr | Ile | Leu | Val | Ser | Ala | Thr | Ser | Leu | Ile | Thr | Pro |
| | | | 420 | | | | | 425 | | | | | 430 | | |
| Lys | Ser | Thr | Phe | Leu | Thr | Thr | Thr | Lys | Pro | Val | Ser | Leu | Leu | Glu | Ser |
| | | 435 | | | | | 440 | | | | | 445 | | | |
| Thr | Lys | Lys | Thr | Ile | Pro | Glu | Leu | Asp | Gln | Pro | Pro | Lys | Leu | Arg | Gly |
| | 450 | | | | | 455 | | | | | 460 | | | | |
| Val | Leu | Gln | Gly | His | Leu | Glu | Ser | Ser | Arg | Asn | Asp | Pro | Phe | Leu | His |
| 465 | | | | | 470 | | | | | 475 | | | | | 480 |
| Pro | Asp | Phe | Cys | Cys | Leu | Leu | Pro | Leu | Gly | Phe | Tyr | Val | Leu | Gly | Leu |
| | | | | 485 | | | | | 490 | | | | | 495 | |
| Phe | Trp | Leu | Leu | Phe | Ala | Ser | Val | Val | Leu | Ile | Leu | Leu | Leu | Ser | Trp |
| | | | 500 | | | | | 505 | | | | | 510 | | |
| Val | Gly | His | Val | Lys | Pro | Gln | Ala | Leu | Asp | Ser | Gly | Gln | Gly | Ala | Ala |
| | | 515 | | | | | 520 | | | | | 525 | | | |
| Leu | Thr | Thr | Ala | Thr | Gln | Thr | Thr | His | Leu | Glu | Leu | Gln | Arg | Gly | Arg |
| | 530 | | | | | 535 | | | | | 540 | | | | |
| Gln | Val | Thr | Val | Pro | Arg | Ala | Trp | Leu | Leu | Phe | Leu | Arg | Gly | Ser | Leu |
| 545 | | | | | 550 | | | | | 555 | | | | | 560 |
| Pro | Thr | Phe | Arg | Ser | Ser | Leu | Phe | Leu | Trp | Val | Arg | Pro | Asn | Gly | Arg |
| | | | | 565 | | | | | 570 | | | | | 575 | |
| Val | Gly | Pro | Leu | Val | Ala | Gly | Arg | Arg | Pro | Ser | Ala | Leu | Ser | Gln | Gly |
| | | | 580 | | | | | 585 | | | | | 590 | | |
| Arg | Gly | Gln | Asp | Leu | Leu | Ser | Thr | Val | Ser | Ile | Arg | Tyr | Ser | Gly | His |
| | | 595 | | | | | 600 | | | | | 605 | | | |
| Ser | Leu | | | | | | | | | | | | | | |
| | 610 | | | | | | | | | | | | | | |

MUTATIONS IN THE GENE ENCODING THE ALPHA CHAIN OF PLATELET GLYCOPROTEIN IB

This invention was made with support under National Heart, Lung, and Blood Institute Grant No. HL32853 and National Cancer Institute Grant No. CA42500 of the National Institutes of Health. Accordingly, the U.S. Government has certain rights in the invention.

This application is a division, of application Ser. No. 07/770,968, filed Oct. 7, 1991, now U.S. Pat. No. 5,317,097.

TECHNICAL FIELD

This invention relates to the α chain of the platelet glycoprotein Ib (GP Ibα). More particularly, the invention relates to mutations in the gene encoding GP Ibα which render the glycoprotein more reactive with von Willebrand factor. Mutant polypeptides and their production and use are provided, with the preferred mutation being at residue Gly 233 of wild-type GP Ibα.

BACKGROUND OF THE INVENTION

Throughout this application various publications are referenced by arabic numerals within parentheses. Full citations for these references may be found at the end of the specification immediately preceding the Sequence Listing. The disclosures of these publications in their entireties are hereby incorporated by reference in this application in order to more fully describe the state of the art to which the invention pertains.

Platelet-type von Willebrand disease (PT-vWD) is an autosomal dominant bleeding disorder in which patients characteristically show prolonged bleeding times, borderline thrombocytopenia, and decreased von Willebrand factor (vWF) high molecular weight multimers and functional activity (1–5). PT-vWD appears to result from an abnormality of the platelet receptor for vWF, whereby patient platelets show an abnormally increased binding of circulating vWF. In the laboratory, this platelet hyperresponsiveness may be demonstrated with the use of low concentrations of ristocetin. Whereas normal platelets show little or no aggregation at ristocetin concentrations as low as 0.5 mg/ml, patient platelets typically show significant binding of vWF, together with strong aggregation, following stimulation by 0.5 mg/ml, or even lower, concentrations of ristocetin (1–3). The unique ability of desialylated vWF (asialo-vWF) to agglutinate patient platelets in the presence of the divalent-cation chelator EDTA has additionally been demonstrated (6). Platelets from patients with PT-vWD also show a characteristically increased binding of the monoclonal antibody C-34, which is directed against an epitope within the platelet glycoprotein (GP) Ib/IX complex (7). Although this complex is known to constitute the platelet's ristocet-independent receptor for vWF (8), identification of a unique structural abnormality within this complex that might underlie the functional abnormalities seen in PT-vWD had not yet been achieved.

The platelet GP Ib/IX receptor for vWF is believed to consist of a 1:1 heterodimeric complex (9) between GP Ib (160 kDa) and GP IX (17 kDa) in a noncovalent association. GP Ib in turn consists of a disulfide-linked 140-kDa α chain (GP Ibα) and 22-kDa β chain (GP Ibβ) (10). A full-length cDNA for GP Ibα was isolated from human erythroleukemia (HEL) cells by Lopez et al. (11). Absolute identity of the HEL GP Ibα sequence with that obtained from the sequencing of nearly 800 nucleotides of cDNA obtained from human platelets was subsequently reported by Wicki et al. (12). Moreover, the human gene for GP Ibα has now been sequenced, and the entire coding region for the resulting protein has been shown to reside within a single exon (13,14).

Functional studies utilizing the water-soluble, extracellular portion of GP Ibα termed glycocalicin, and more particularly the 45-kDa amino-terminal region common both to glycocalicin and to the native GP Ibα molecule, strongly suggest that the actual binding of vWF occurs within this region (15–18). What roles the other constituents of the complex may play in the regulation of vWF binding to the receptor remain unknown.

Previous investigations of the substitution of single amino acids at critical positions in protein sequences have demonstrated significant changes in the three-dimensional structure of these proteins (39). For example, substitution of Val (or any non-cyclic L-amino acid) for Gly 12 in the ras-oncogene-encoded p21 protein results in local changes in the conformation of the protein that result in more global changes in the protein structure (39,40). This alteration in structure is associated with activation of the protein (39,40).

It is known that the linear sequence of amino acids in a protein determines its three-dimensional structure of conformation (41–44). This conformation is the one of lowest conformational energy (41–44). This principle allows computation of the structure of a polypeptide from its amino acid sequence. It is possible to compute the conformational energy for a particular conformation of a polypeptide using an equation which has been parameterized on a large body of experimental crystal structure and gas phase data and is contained in the computer program ECEPP (Empirical Conformational Energies of Peptides Program) (43). It is possible to generate the conformations that can be adopted by a given polypeptide chain. The conformational energies for each of these conformers is computed and then subjected to energy minimization (39,41). The resulting lowest energy conformer(s) is (are) then the one(s) that should be observed experimentally. The program ECEPP has been used to compute the low energy conformations for the single amino acid residues (45,46), oligopeptides (47), polypeptides such as gramicidin s and collagen (48,49), and proteins such as melittin (50), and arian pancreatic polypeptide, with excellent agreement between the predicted low energy structures and the corresponding experimentally determined ones (39, 41,42).

It has been shown that the conformational preferences of an amino acid residue in a polypeptide chain are predominantly influenced by its four nearest neighbors on the amino and carboxyl terminal ends of this residue (51).

SUMMARY OF THE INVENTION

Platelet-type von Willebrand disease (PT-vWD) is an autosomal dominant bleeding disorder characterized by abnormally enhanced binding of von Willebrand factor (vWF) by patient platelets. Although the platelet glycoprotein (GP) Ib/IX complex is known to constitute the platelet's ristocetin-dependent receptor for vWF, a unique structural abnormality within this complex had not previously been identified in PT-vWD. Using the polymerase chain reaction to amplify genomic DNA coding for the α chain of GP Ib (GP Ibα) and then sequencing the amplified DNA following cloning into M13mp18 and M13mp19 phage vectors, we have found a single point mutation in the GP Ibα coding region of PT-vWD DNA resulting in the substitution of valine for glycine at residue 233. This substitution within the vWF-binding region of GP Ibα is likely to exert a significant influence on the conformation of the resulting protein. Competitive oligonucleotide primer (COP) assay for this mutation showed a homozygous wild-type pattern in genomic DNA from the 161 normal volunteers studied and from 6 phenotypically normal members of a PT-vWD family. All 7 affected members of this family studied were heterozygous for the mutant allele. Platelet GP Ibα mRNA reverse-transcribed and studied by competitive oligonucleotide primer assay showed similar expression of the mutant and wild-type alleles in the affected PT-vWD patients. Absence in the normal population, tight linkage with phenotypic expression of disease, and absence of any additional abnormality of GP Ibα in these patients identify the glycine-to-valine substitution as a point mutation underlying functional abnormality of the vWF receptor in PT-vWD.

To investigate the effect of this substitution on the three-dimensional structure of this region of the protein, we have generated the allowed (low energy) conformations of the region of the GP Ibα protein containing residues 228–238 (with 5 residues on either side of the critical residue 233) with Gly 233 (wild type) and Val 233 (PT-vWD) using the computer program ECEPP (Empirical Conformational Energies of Peptides Program). The wild-type sequence is Tyr-Val-Trp-Lys-Gln-Gly-Val-Asp-Val-Lys-Ala (SEQUENCE ID NO: 9). We find that the Gly 233-containing peptide can exist in two low energy conformers. The lowest energy conformer is a structure containing a β-turn at Gln 232-Gly 233 while the alternative conformation is an amphipathic helical structure. Only the amphipathic helical structure is allowed for the Val 233-containing peptide which contains a hydrophobic 'face' consisting of Val 229, Val 233 and Val 236 and another hydrophilic surface composed of such residues as Lys 231 and Asp 235. No such surfaces exist for the lowest energy bend conformer for the Gly 233-containing peptide, but do exist in the higher energy helical structure. The amphipathic surfaces in the 228–238 region of the Val 233-containing GP protein may associate strongly with complementary surfaces during vWF binding to the GPIb/IX receptor complex and may help explain heightened association of vWF with this receptor in PT-vWD.

It is thus an object of the present invention to determine a structural abnormality within GP Ibα itself which underlies PT-vWD. From studies at both the genomic DNA and platelet RNA levels, the subject invention provides for a unique point mutation (Val for Gly 233) that results in an abnormality of primary structure of platelet GP Ibα in patients with PT-vWD. It is a further object of the subject invention to provide a recombinant polypeptide having this mutation and methods of producing and using the mutant polypeptide.

It is also an object of the subject invention to determine changes in conformation which occur that are induced in the functional region of the GP Ibα protein by substitution of Val for Gly 233.

BRIEF DESCRIPTION OF THE FIGURES

These and other objects, advantages and features of the present invention will be more fully understood from the following detailed description of certain embodiments thereof when considered in conjunction with the accompanying drawings in which.

DETAILED DESCRIPTION OF THE INVENTION

Figure 1:
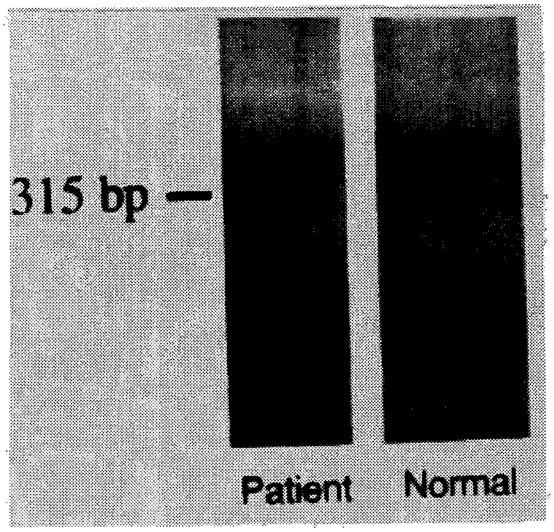
FIG. 1 shows amplification of GP Ibα genomic DNA. The PCR primer pair J9/J10 (SEQUENCE ID NO: 3 and SEQUENCE ID NO: 4, respectively) was used to amplify nucleotides 737–1051 of the genomic DNA of patient II-2 or a normal individual. After electrophoresis in a 1% agarose gel, amplified products of 315 base pairs (bp) are seen by ethidium bromide staining in each case.

The subject invention provides a purified polypeptide encoded by a DNA sequence, the DNA sequence comprising DNA encoding naturally-occurring wild-type platelet glycoprotein Ib alpha (GP Ibα) having a mutation which renders the polypeptide encoded by the DNA more reactive with von Willebrand factor. All the references to map positions correspond to the identically numbered positions along the amino acid sequence of GP Ibα shown on page 4 of European Patent Application Publication No. 0 317 278 A2, published May 24, 1989, and/or page 5617 of the Proc. Natl. Acad. Sci. USA article by J. A. Lopez et al., volume 84, pages 5615–5619, the contents of each of which are hereby incorporated into the subject application in their entireties. The European Application is entitled "Proteolytic fragments and synthetic peptides that block the binding of von Willebrand factor to the platelet membrane glycoprotein Ib" and was filed on behalf of Scripps Clinic and Research, with T. S. Zimmerman et al. listed as inventors. The sequence shown on page 4 of the European Application represents the sequence of the first 293 amino acids of naturally-occurring wild-type platelet glycoprotein Ib alpha. The article by Lopez et al. is entitled "Cloning of the α chain of human platelet glycoprotein Ib: A transmembrane protein with homology to leucine-rich $\alpha_2$-glycoprotein" and provides the amino acid sequence for the remainder of the GP Ibα protein. The amino acid sequence of the naturally-occurring wild-type platelet glycoprotein Ib alpha is also given below:

SEQ ID NO:11:

His Pro Ile Cys Glu Val Ser Lys Val Ala Ser His Leu Glu Val Asn
5 10 15

Cys Asp Lys Arg Asn Leu Thr Ala Leu Pro Pro Asp Leu Pro Lys Asp
20 25 30

Thr Thr Ile Leu His Leu Ser Glu Asn Leu Leu Tyr Thr Phe Ser Leu
35 40 45

Ala Thr Leu Met Pro Tyr Thr Arg Leu Thr Gln Leu Asn Leu Asp Arg
50 55 60

Cys Glu Leu Thr Lys Leu Gln Val Asp Gly Thr Leu Pro Val Leu Gly
65 70 75 80

Thr Leu Asp Leu Ser His Asn Gln Leu Gln Ser Leu Pro Leu Leu Gly
85 90 95

Gln Thr Leu Pro Ala Leu Thr Val Leu Asp Val Ser Phe Asn Arg Leu
100 105 110

Thr Ser Leu Pro Leu Gly Ala Leu Arg Gly Leu Gly Glu Leu Gln Glu
115 120 125

Leu Tyr Leu Lys Val Asn Glu Leu Lys Thr Leu Pro Pro Gly Leu Leu
130 135 140

Thr Pro Thr Pro Lys Leu Glu Lys Leu Ser Leu Ala Asn Asn Asn Leu
145 150 155 160

Thr Glu Leu Pro Val Gly Leu Leu Asn Gly Leu Glu Asn Leu Asp Thr
165 170 175

Leu Leu Leu Gln Glu Asn Ser Leu Tyr Thr Ile Pro Lys Gly Phe Phe
180 185 190

Gly Ser His Leu Leu Pro Phe Ala Phe Leu His Gly Asn Pro Trp Leu
195 200 205

Cys Asn Cys Glu Ile Leu Tyr Phe Arg Arg Trp Leu Gln Asp Asn Ala
210 215 220

Glu Asn Val Tyr Val Trp Lys Gln Gly Val Asp Val Lys Ala Met Thr
225 230 235 240

Ser Asn Val Ala Ser Val Gln Cys Asp Asn Ser Asp Lys Phe Pro Val
245 250 255

Tyr Lys Tyr Pro Gly Lys Gly Cys Pro Thr Leu Gly Asp Glu Gly Asp
260 265 270

Thr Asp Leu Tyr Asp Tyr Tyr Pro Glu Glu Asp Thr Glu Gly Asp Lys
275 280 285

Val Arg Ala Thr Arg Thr Val Val Lys Phe Pro Thr Lys Ala His Thr
290 295 300

-continued

Thr Pro Trp Gly Leu Phe Tyr Ser Trp Ser Thr Ala Ser Leu Asp Ser
305 310 315 320

Gln Met Pro Ser Ser Leu His Pro Thr Gln Glu Ser Thr Lys Glu Gln
325 330 335

Thr Thr Phe Pro Pro Arg Trp Thr Pro Asn Phe Thr Leu His Met Glu
340 345 350

Ser Ile Thr Phe Ser Lys Thr Pro Lys Ser Thr Thr Glu Pro Thr Pro
355 360 365

Ser Pro Thr Thr Ser Glu Pro Val Pro Glu Pro Ala Pro Asn Met Thr
370 375 380

Thr Leu Glu Pro Thr Pro Ser Pro Thr Thr Pro Glu Pro Thr Ser Glu
385 390 395 400

Pro Ala Pro Ser Pro Thr Thr Pro Glu Pro Thr Pro Ile Pro Thr Ile
405 410 415

Ala Thr Ser Pro Thr Ile Leu Val Ser Ala Thr Ser Leu Ile Thr Pro
420 425 430

Lys Ser Thr Phe Leu Thr Thr Thr Lys Pro Val Ser Leu Leu Glu Ser
435 440 445

Thr Lys Lys Thr Ile Pro Glu Leu Asp Gln Pro Pro Lys Leu Arg Gly
450 455 460

Val Leu Gln Gly His Leu Glu Ser Ser Arg Asn Asp Pro Phe Leu His
465 470 475 480

Pro Asp Phe Cys Cys Leu Leu Pro Leu Gly Phe Tyr Val Leu Gly Leu
485 490 495

Phe Trp Leu Leu Phe Ala Ser Val Val Leu Ile Leu Leu Leu Ser Trp
500 505 510

Val Gly His Val Lys Pro Gln Ala Leu Asp Ser Gly Gln Gly Ala Ala
515 520 525

Leu Thr Thr Ala Thr Gln Thr Thr His Leu Glu Leu Gln Arg Gly Arg
530 535 540

Gln Val Thr Val Pro Arg Ala Trp Leu Leu Phe Leu Arg Gly Ser Leu
545 550 555 560

Pro Thr Phe Arg Ser Ser Leu Phe Leu Trp Val Arg Pro Asn Gly Arg
565 570 575

Val Gly Pro Leu Val Ala Gly Arg Arg Pro Ser Ala Leu Ser Gln Gly
580 585 590

Arg Gly Gln Asp Leu Leu Ser Thr Val Ser Ile Arg Tyr Ser Gly His
595 600 605

Ser Leu
610

The polypeptides of the subject invention have a mutation in this naturally-occurring sequence which renders the mutant polypeptide more reactive with von Willebrand factor. This increased reactivity, or hyperresponsiveness, can be demonstrated in the laboratory using low concentrations of ristocetin. Any other suitable means for determining the reactivity of the polypeptide with vWF can also be utilized to identify polypeptides which are "more" reactive with vWF, i.e. more reactive than naturally-occurring wild-type GP Ibα.

In one embodiment of the subject invention, the mutation occurs within a hinge region of the DNA encoding the naturally-occurring wild-type platelet GP Ibα. The "hinge" region is defined as the region including residues 220 to 310. GP Ibα has a leucine rich area from residue 36 to residue 200. Residues 200 to about 220 represent a flanking region to the leucine rich area. A similar flanking region of about 22 residues is found on the amino-terminal side of the leucine rich area. Residues 310 to residue 420 represent a serine/threonine rich area. The residues lying between the flanking region of the leucine rich area (on the leucine rich area's carboxy terminal side) and the serine/threonine rich area represent the "hinge" region (residues 220 to 310). This hinge region is a major binding site for vWF within the GP Ibα protein.

By utilizing energy conformational analysis of the GP Ibα mutant of the subject invention, applicants have determined that residues 228 to 238 within this hinge region are preferred sites for mutations that result in a mutant polypeptide having more reactivity with vWF. This is discussed in further detail below. Preferably, the mutation is at residue 233 within the hinge region, which in the wild-type GP Ibα encodes glycine. A substitution of valine for glycine 233 is preferred, but other amino acids could also be substituted as also discussed in further detail below.

In one embodiment of the subject invention, the mutation alters the three-dimensional structure of the polypeptide from a beta bend conformation to an alpha helix conformation at the mutation. The alpha helix conformation represents the mutant polypeptide's lowest energy conformation. In an additional embodiment, the mutation produces an amphipathic region within the polypeptide, with the polypeptide with the amphipathic region being the polypeptide's lowest energy conformation. An amphipathic region is an area having both a hydrophobic and a hydrophilic region within the protein. The hydrophobic region plays a role in the increased reactivity with vWF as discussed below. The polypeptide's lowest energy conformation as used herein relates to this eleven amino acid portion (amino acids 228 to 238). In this portion, the wild type conformation is not an alpha helix or amphipathic at its lowest energy conformation.

This eleven amino acid portion can be further stabilized as an alpha helix by adding four glutamic acid residues at the amino terminal and four lysine residues at the carboxy terminal of the eleven amino acids. These additional highly charged amino acids exert a stabilizing effect on the alpha helix.

The polypeptides of the subject invention can be used as compositions (including pharmaceutical compositions) comprising an amount of the polypeptide effective to inhibit platelet adhesion/aggregation and a compatible carrier (pharmaceutically acceptable carrier for pharmaceutical compositions). For the purposes of this application, "platelet adhesion/aggregation" is a term which includes adhesion of platelets to a non-platelet surface; adhesion of platelets to other platelets; and aggregation of platelets to other platelets. Due to their increased reactivity, the mutant polypeptides readily bind to vWF and essentially neutralize the "stickiness" of the vWF by saturating the available binding sites on the vWF molecule. Platelets are then unable to bind to the vWF and platelet adhesion/aggregation is thus inhibited. This property can be utilized to inhibit platelet aggregation, to inhibit thrombus formation, and in the production of medical devices which may cause adhesion/aggregation of platelets at the location of the medical device within a subject. In the case of the medical device, the device is coated with the mutant polypeptides of the subject invention. Due to the increased reactivity of the mutant polypeptides with vWF, circulating vWF binds to the mutant polypeptide coated onto the medical device. Circulating platelets are thus prevented from aggregating at the location of the medical device. This platelet adhesion/aggregation concept can also be utilized within human blood vessels, whereby coating of the vessel wall or an artificial shunt within the vessel with the mutant polypeptide can inhibit adhesion/aggregation of platelets at the vessel wall or at the artificial shunt. Numerous other applications utilizing this inhibition of platelet adhesion/aggregation property would be readily apparent to those skilled in the art to which the subject invention pertains. One such application is in the inhibition of thrombus formation.

The polypeptides of the subject invention could also be labeled with a detectable marker, and used as imaging agents. The marker could be a radioactive isotope, an element opaque to X-rays, or a paramagnetic ion. Radioactive isotopes are commonly used in medicine and are well known to those skilled in the art. Representative examples include indium-111, technetium-99m, and iodine-123. Paramagnetic ions are also commonly used in medicine and include, for example, chelated metal ions of chromium (III), manganese (II), and iron (III). Imaging can be done through any of the methods known to those skilled in the art. These methods include but are not limited to X-ray, CAT scan, PET scan, NMRI, and fluoroscopy.

Similarly, the polypeptide can be bound to a thrombolytic agent, such as tissue plasminogen activator (TPA), urokinase, Streptokinase, prourokinase, Anisoylated Plasminogen-Streptokinase Activator Complex (Eminase™), TPA analogs, or a protease. The mutant polypeptides bound to a thrombolytic agent can be utilized to localize the thrombolytic agent to the site of a thrombus formation. As used in this application, "bound" encompasses polypeptides bound covalently, non-covalently, or conjugated. The polypeptides may be conjugated through other chemical moieties, including amino acid or polypeptide cross-linkers, which are standardly used in the art and are well known to those skilled in the art to which the invention pertains.

The subject invention provides nucleic acid molecules encoding the polypeptides of this invention, including cDNA and isolated genomic DNA. DNA encoding the mutant polypeptides of the subject invention can be isolated from PT-vWD patients, as discussed below. DNA encoding the mutant polypeptides can also be obtained by subjecting wild-type GP Ibα DNA to various procedures to generate the desired mutation therein. Such procedures are readily apparent to those skilled in the art, and include, for example, site-directed mutagenesis.

The mutant DNA can be utilized to express the mutant polypeptides in various host cells. Suitable host cells are any cells in which the DNA sequence encoding the mutant polypeptide has been introduced by recombinant DNA techniques, as long as the cell is capable of expressing the DNA sequence and producing the polypeptide product. The cell may be a bacterial cell, an insect cell, a yeast cell, a mammalian cell such as Chinese hamster ovary cells, or any other suitable cell. Suitable bacterial cells include *Escherichia coli* and *Pseudomonas aeruginosa,* as well as *Bacillus subtilis.* Suitable insect cells include SF9 or SF21 cells.

The host cells may contain the sequence encoding the mutant polypeptide in the body of a vector, such as a plasmid or a viral vector. The plasmid or vital vector is constructed by recombinant DNA techniques so that the sequence encoding the mutant polypeptide is incorporated at a suitable position in the molecule.

Specifically, a plasmid for expression of the polypeptide may comprise DNA encoding the polypeptide and DNA encoding suitable regulatory elements positioned relative to the DNA encoding the polypeptide so as to effect expression of the polypeptide in a suitable host cell. Plasmids and viral vectors can harbor a variety of suitable regulatory elements, including promoters and operators, ribosomal binding sites, and repressors.

A preferred viral vector for use with an insect host cell is the Baculovirus expression vector system. The Baculovirus expression vector system is described in detail in U.S. Pat. No. 4,745,051, issued May 17, 1988 (G. E. Smith and M. D. Summers, "Method For Producing A Recombinant Baculovirus Expression Vector") and U.S. Pat. No. 4,879,236, issued Nov. 7, 1989 (G. E. Smith and M. D. Summers, "Method For Producing A Recombinant Baculovirus Expression Vector"), the contents of each of which are hereby incorporated by reference into the subject application. "A Manual of Methods for Baculovirus Vectors and Insect Cell Culture Procedures" by M. D. Summers and G. E. Smith (1987, 1988 Texas Agricultural Station, College Station, Tex.) is also readily available to those skilled in the art and provides a practical laboratory description on how to utilize the Baculovirus expression vector system.

The subject invention thus also provides a baculovirus vector for expression of the mutant polypeptides which comprises the DNA encoding the polypeptide and DNA encoding suitable regulatory elements positioned relative to the DNA encoding the polypeptide so as to effect expression of the polypeptide in a suitable host cell. In the case of the baculovirus vector, the suitable host cell comprises an insect cell.

In general, the subject invention thereby provides a method of producing the mutant polypeptides which comprises expressing DNA encoding the polypeptide in a suitable host so that the polypeptide is produced, recovering the polypeptide so produced from the host, and purifying the polypeptide so recovered.

The invention also provides probes suitable for hybridizing to the DNA encoding the mutant polypeptide. Specifically, the invention provides a DNA oligomer comprising a DNA sequence complementary to DNA encoding naturally-occurring wild-type platelet glycoprotein Ib alpha having a mutation which renders the polypeptide encoded by the DNA more reactive with von Willebrand factor. As with the polypeptides of the subject invention, the DNA oligomer preferably comprises a complementary sequence which is complementary to a hinge region of the DNA encoding the naturally-occurring wild-type platelet glycoprotein Ib alpha (amino acids 220 to 310). Amino acids 228 to 238, and specifically amino acid 233, are the preferred sites for mutations within the hinge region. At amino acid 233, the substitution of valine for the glycine present in the wild-type GP Ibα is preferred, resulting in a DNA oligomer having the complementary sequence (SEQUENCE ID NO:6):

5' AAGCAAGTTGTGGACG -3'.

The DNA oligomer can be labeled with a detectable marker, such as a radiolabeled molecule, a fluorescent molecule, an enzyme, a ligand, or biotin. The labeled oligomer can then be utilized to detect a mutation in the DNA encoding naturally-occurring wild-type platelet glycoprotein IB alpha so as to diagnose platelet-type von Willebrand disease. This method comprises:

a) obtaining a blood sample from the subject;

b) treating the blood sample so as to expose DNA present in the blood sample;

c) contacting the exposed DNA with the labeled DNA oligomer under conditions permitting hybridization of the DNA oligomer to any DNA complementary to the DNA oligomer present in the blood sample, the DNA complementary to the DNA oligomer containing the mutation;

d) removing unhybridized, labeled DNA oligomer; and e) detecting the presence of any hybrid of the labeled DNA oligomer and DNA complementary to the DNA oligomer present in the blood sample, thereby detecting the mutation and diagnosing platelet-type von Willebrand disease.

METHODS

Subjects. We studied three generations of a previously described (1,4) Caucasian family with PT-vWD. For all patients undergoing genetic analysis, presence or absence of the PT-vWD phenotype was assessed. The unique agglutination of patient platelet-rich plasma induced by asialo-vWF in the presence of 5 mM EDTA (6) was used to identify presence of the disease. Family members showing evidence of PT-vWD were clearly segregated from unaffected relatives by this test, with no equivocal results.

The normal population that was studied comprised 161 adults, all of whom denied any history of an increased bleeding tendency. This population consisted of 70 medical students and 91 hospital personnel, representing a variety of ethnic backgrounds, although predominantly Caucasian. Informed consent for these studies was given by each subject, as approved by the Institutional Review Board for the Protection of Human Subjects at the State University of New York Health Science Center at Syracuse.

Preparation and Analysis of DNA and Platelet RNA. Peripheral blood leukocytes were used as a source of genomic DNA. For our initial studies, 50 ml of blood was drawn, and DNA was purified by standard techniques (19, 20). DNA for use in the competitive oligonucleotide primer (COP) assay (see below) was isolated from 5–10 ml of peripheral blood by the method of Kawasaki (21). Total RNA was isolated from the platelets present in 50–100 ml of blood by using a guanidinium isothiocyanate/cesium chloride gradient as described (22).

Polymerase Chain Reaction (PCR). Genomic DNA was amplified by the PCR using a series of oligonucleotide primer pairs. Since the entire coding region of the resulting protein is contained within a single exon (13,14), nucleotide positions corresponding to the GP Ibα cDNA sequence (11) have been used in the present study. The PCR primers are listed in Table 1. PCR amplifications were performed for 30–40 cycles in an Eppendorf Microcycler, with annealing at 55°–60° C. for 30–60 seconds, extension at 72° C. for 2 minutes, and denaturation at 94° C. for 30 seconds. To 100 μl of reaction Buffer, 1 μg of genomic DNA, 2.5 units of Taq DNA polymerase (Perkin-Elmer/Cetus), 50 pmol of each primer, and 10 nmol of each dNTP were added. DNA amplified by PCR was subsequently cloned into M13mp18 and M13mp19 bacteriophage.

DNA Sequence Analysis. Complete sequence of the GP Ibα coding region (nucleotides 91–1920) was obtained by a combination of (i) standard dideoxy sequencing (23) of PCR products cloned into M13mp18 and M13mp19 with (ii) direct sequencing of PCR products by the method of Carothers et al. (24). Since the autosomal dominant genetics of PT-vWD suggested that any abnormality would be heterozygous, at least 9 individual clones and a pool of 30 or more clones were sequenced for each region that was read from cloned DNA. Oligonucleotide primer pairs and the amino acid residues of GP Ibα included in the

TABLE I

Oligonucleotide PCR Primers

| Primer | Nucleotides included* | Direction | Sequence | Amino acids included** |
|---|---|---|---|---|
| J8 | 38–60 | Sense | 5'-TACTGAATTCCTCATGCCTCTCCTCCTCTTG-3' (SEQUENCE ID NO: 1) | −16–222 |
| J5A | 758–728 | Antisense | 5'-TTGTCCTGCAGCCAGCGACGAAAATAGAGGA-3' (SEQUENCE ID NO: 2) | |
| J9 | 737–753 | Sense | 5'-TTCGTCGCTGGCTGCAG-3' (SEQUENCE ID NO: 3) | 217–320 |
| J10 | 1051–1035 | Antisense | 5'-GGCTGTCTAGAGAAGCA-3' (SEQUENCE ID NO: 4) | |
| J12 (or J13) | 781–796 | Sense | 5'-AAGCAAGG(or T)TGTGGACG-3' (SEQUENCE ID NO: 5 and SEQUENCE ID NO: 6, respectively) | 231–320 |
| J10 | 1051–1035 | Antisense | 5'-GGCTGTCTAGAGAAGCA-3' (SEQUENCE ID NO: 4) | |
| J6 | 748–777 | Sense | 5'-CTGCAGGACAATGCTGAAAATGTCTACGTA-3' (SEQUENCE ID NO: 7) | 220–610 |
| J14 | 1987–1964 | Antisense | 5'-CCGGATCCCAACTAGATTCCAATAGGAGAG-3' (SEQUENCE ID NO: 8) | |

*The J8 primer additionally has sequence 5' to nucleotide 38 that includes an EcoRI recognition site, and the J14 primer has sequence 3' to nucleotide 1987 that includes a BamHI recognition site.
**The J8/J5A primer pair includes the GP Ibα signal peptide (−16 to −1) in addition to residues 1–222 of the mature protein.

amplified PCR products are shown in Table 1.

GP Ibα DNA sequence for nucleotides 80–727 and 754–1034 was read from cloned DNA amplified with primer pairs J8/J5a (SEQUENCE ID NO: 1 and SEQUENCE ID NO: 2, respectively) and J9/J10 (SEQUENCE ID NO: 3 and SEQUENCE ID NO: 4, respectively), respectively. Direct sequencing of DNA amplified with primer pair J8/J10 (SEQUENCE ID NO: 1 and SEQUENCE ID NO: 4, respectively) provided sequence in the 72-8-753 region for which amplified DNA would reflect the sequence of primers J5A (SEQUENCE ID NO: 2) and J9 (SEQUENCE ID NO: 3) themselves. In addition, direct sequencing of DNA amplified by primer pair J6/J14 (SEQUENCE ID NO: 7 and SEQUENCE ID NO: 8, respectively), which included the remaining sequence of the GP Ibα coding region, proved capable of resolving all but a few difficult reading regions. Cloned DNA containing the full-length GP Ibα coding sequence of both the wild-type and mutant alleles was obtained using J8 (SEQUENCE ID NO: 1) and J14 (SEQUENCE ID NO: 8) as a PCR primer pair later in the course of these studies. This cloned DNA provided definitive resolution and confirmation of sequence for those remaining regions in which analysis by direct sequencing had been difficult.

COP Assay. COP analysis (25) was developed for population screening for the presence of a single nucleotide point mutation. In brief, the 16-met oligonucleotide sense primers J12 (SEQUENCE ID NO: 5) and J13 (SEQUENCE ID NO: 6), each differing by only a single base at position 8, were utilized in equimolar concentrations as competing primers in a PCR reaction, with J10 (SEQUENCE ID NO: 4) serving as a common antisense primer. To approximately 5 μg of genomic DNA were added 50 pmol each of primers J12 (SEQUENCE ID NO: 5), J13 (SEQUENCE ID NO: 6), and J10 (SEQUENCE ID NO: 4) and 12.5 nmol of each dNTP in a total volume of 100 μl. For each individual studied, the COP assay was run in duplicate: to one tube was added a trace amount (≈$8\times10^5$ cpm) of $^{32}$P-labeled J12 (SEQUENCE ID NO: 5), and to the other tube an equivalent amount of $^{32}$P-labeled J13 (SEQUENCE ID NO: 6). This technique was also applied to platelet RNA, as follows. The J9/J10 (SEQUENCE ID NO: 3 and SEQUENCE ID NO: 4, respectively) primer pair was used in the sequential reverse transcription and PCR amplification of platelet RNA (22). The PCR mixture was then diluted 1:50 with 0.1 mM EDTA/10 mM Tris hydrochloride, pH 7.4, and 10 μl of this diluted material was then used as the target for a subsequent COP procedure, with the addition of 50 pmol each of J12 (SEQUENCE ID NO: 5) and J13 (SEQUENCE ID NO: 6) as well as an additional 50 pmol of J10 (SEQUENCE ID NO: 4). Tracer amounts of $^{32}$P-labeled J12 (SEQUENCE ID NO: 5) or J13 (SEQUENCE ID NO: 6) were added as in the case of genomic DNA COP analyses. COP amplifications were performed for 25 PCR cycles for genomic DNA and 15 cycles for reverse-transcribed platelet RNA. Annealing was at 49° C. for 60 seconds, followed by extension at 72° C. for 3 minutes and denaturation at 94° C. for 45 seconds. Amplified products from the COP reactions were electrophoresed in agarose gels containing 2.5% NuSieve GTG agarose (FMC) and 1% low-electroendosmosis (EEO) agarose (Boehringer Mannheim). After electrophoresis, the gels were dried and autoradiography was performed.

Linkage Analysis. Logarithm-of-odds (lod) scores (26) for assessment of linkage between PT-vWD phenotypic expression and allele assignments resulting from DNA analysis were computed using the MENDEL program (27).

RESULTS

The nearly intronless nature of the gene coding for platelet GP Ibα (13,14) permitted our initial studies to be performed on genomc DNA obtained from the circulating leukocytes of PT-vWD patients. Using a series of oligonucleotide PCR primer pairs (Table 1), we observed identically migrating bands of amplified DNA from patients as compared with normal controls (FIG. 1). This finding suggested the absence of any major deletions Within the gene but could not exclude the possibility of alterations affecting only one or several nucleotides within the amplified segments.

Figure 2A:
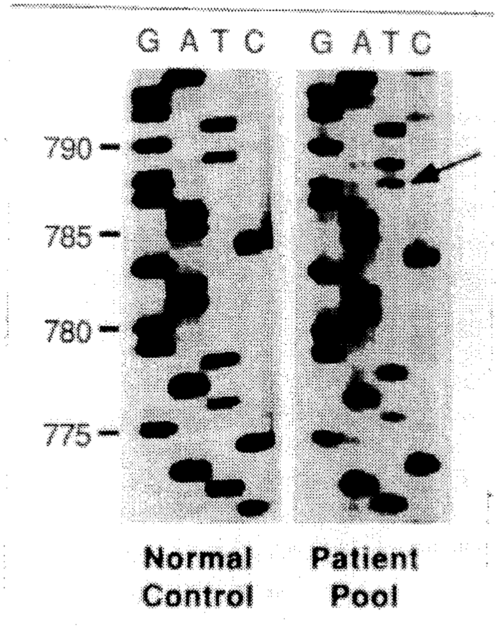
FIGS. 2A and 2B show DNA sequence analysis of the GP Ibα gene in PT-vWD. Genomic DNA amplified by the primer pair J9/J10 (SEQUENCE ID NO: 3 and SEQUENCE ID NO: 4, respectively) was cloned into M13mp18 and then sequenced. A) Products of sequencing reactions show the heterozygous presence of a G and a T at nucleotide position 788 (arrow) in a pool of 32 individual M13mp18 clones of amplified DNA from patient II-2, in contrast to the homozygous wild-type G seen in a normal individual. B) The corresponding sequences of the wild-type and mutant alleles from individual M13mp18 clones of amplified DNA from this patient are shown.
Figure 2B:
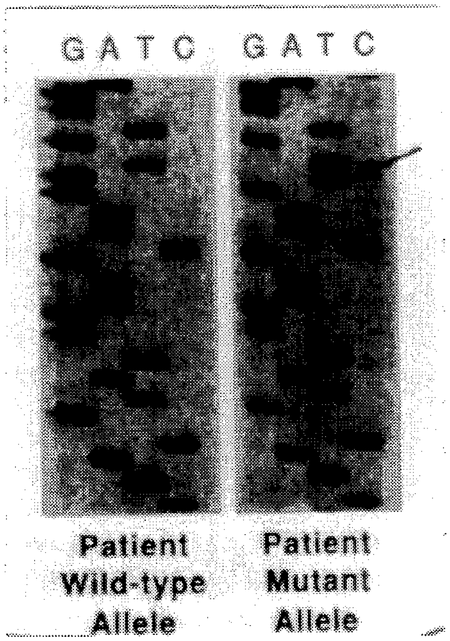

DNA sequencing of two PT-vWD patients confirmed the absence of any substitutions, additions, or deletions of nucleotides, as compared with the normal genome, throughout the entire protein coding region, with a single exception. In both PT-vWD patients, the substitution of T for G at position 788 of the nucleotide sequence was observed. This substitution was nonconservative, resulting in the substitution of valine for glycine at residue 233 of the mature GP Ibα molecule. The G-to-T substitution was heterozygous in the PT-vWD patients (FIG. 2). Only the wild-type G at position 788 was seen in normal individuals.

Figure 3:
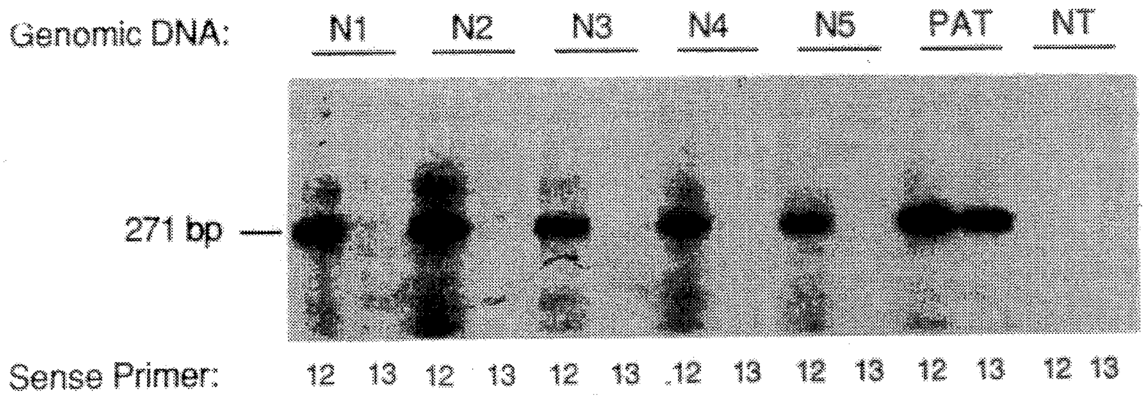
FIG. 3 shows COP assay for mutation in GP Ibα genomic DNA. Genomic DNA samples from each of five normal individuals (N1–N5) and from patient II-5 (PAT), as well as a "no template" control lacking any target DNA (NT), were amplified in parallel PCRs using the sense primers J12 (SEQUENCE ID NO: 5) and J13 (SEQUENCE ID NO: 6) and the antisense primer J10 (SEQUENCE ID NO: 4). Trace amounts of either $^{32}$P-labeled J12 (SEQUENCE ID NO: 5) or $^{32}$P-labeled J13 (SEQUENCE ID NO: 6) were added to each reaction, as noted by a 12 or a 13 below each lane. After 25 PCR cycles, the amplification product was electrophoresed in an agarose gel, the gel was dried, and autoradiography was performed. While ethidium bromide staining demonstrated a band of amplified DNA at 271 bp in all lanes (data not shown), the autoradiograph reveals that the amplified product is composed exclusively of the wild-type allele in all normal controls, but of both the wild-type and mutant alleles in the patient.
Figure 4:
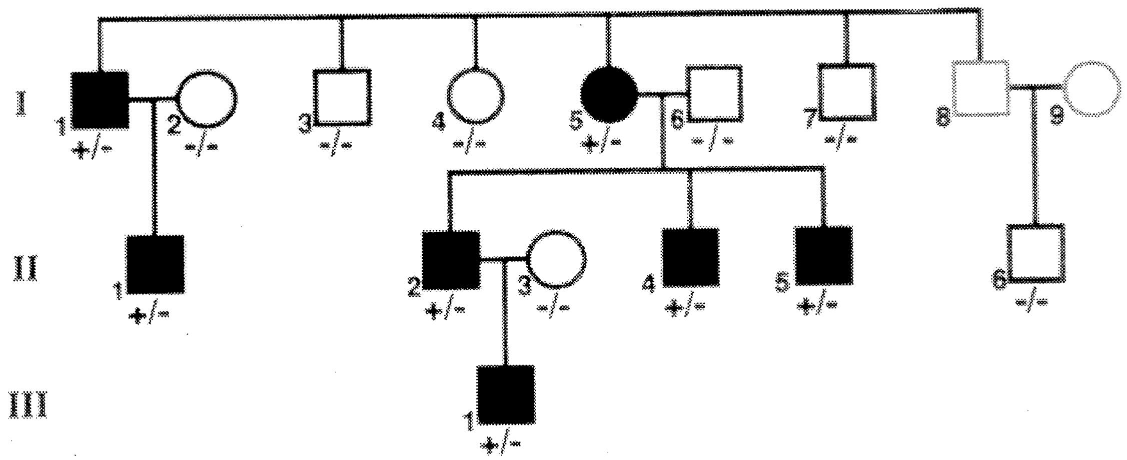
FIG. 4 shows linkage analysis of PT-vWD and mutation of the GP Ibα gene. Solid symbols represent patients showing phenotypic expression of PT-vWD, and open symbols represent family members lacking disease expression. Individuals unavailable for study are shown by gray symbols. Squares denote males, and circles denote females. Based on COP assay results, mutant alleles (coding for valine at residue 233) are represented by plus signs, and wild-type alleles (coding for glycine) by minus signs.

Substitution of T for G at position 788 did not create or destroy a recognition sequence for any known restriction enzyme. To investigate the occurrence of this substitution in a large number of individuals, we developed a screening assay based on the COP technique reported by Gibbs et al. (25). Using equal amounts of J12 (SEQUENCE ID NO: 5) and J13 (SEQUENCE ID NO: 6) and only a trace amount of either $^{32}$P-labeled J12 (SEQUENCE ID NO: 5) or $^{32}$P-labeled J13 (SEQUENCE ID NO: 6), we sought to identify the presence of alleles showing a perfect match with the individual primers. The COP technique correctly identified the presence of both alleles in the genomic DNA of all affected PT-vWD patients but identified only the wild-type allele in the genomic DNA of normal individuals (FIG. 3). We subsequently applied this technique to 161 unrelated normal volunteers and observed a homozygous wild-type pattern in each case, for a total of 322 normal alleles. Moreover, the COP assay indicated a homozygous wild-type pattern from the six phenotypically normal members of the PT-vWD family. All seven members of the family for whom phenotypic expression of PT-vWD could be demonstrated were heterozygous for the mutant allele by COP assay (FIG. 4). The association of the heterozygous G-to-T substitution at nucleotide 788 accordingly showed very tight linkage with clinical expression of the PT-vWD phenotype, with a maximum lod score of 2.53 at a recombination fraction of 0.

Figure 5A:
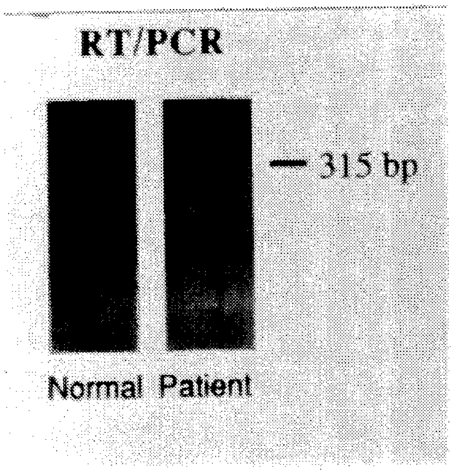
FIGS. 5A and 5B show expression of both mutant and wild-type mRNA in the platelets of PT-vWD patients. Platelet mRNA from patient II-4 or from a normal control was reverse-transcribed (RT) and the resulting cDNA was amplified with the J9/J10 (SEQUENCE ID NO: 3 and SEQUENCE ID NO: 4, respectively) primer pair, producing the anticipated 315-bp products (A). This cDNA was then used as starting material in the COP procedure. Autoradiography of COP products (B) shows the presence of both mutant and wild-type expression in patient platelets, but only wild-type expression in normal platelets.
Figure 5B:
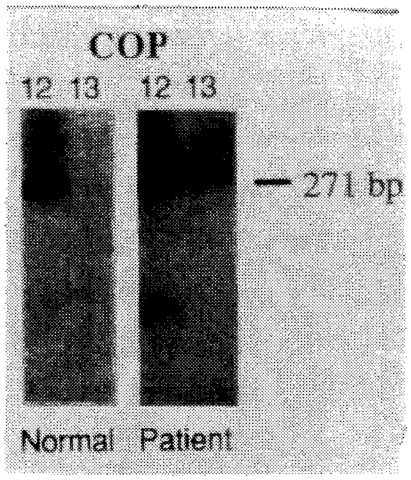

Gene expression was studied by PCR analysis of reverse-transcribed platelet mRNA. As in the case of genomic DNA, no gross deletions were seen in the patient samples (FIG. 5 A). Application of the COP technique to cDNA reverse transcribed from platelet mRNA showed similar expression of the mutant and wild-type alleles in the affected PT-vWD patients (FIG. 5 B). Normal individuals and phenotypically normal members of the PT-vWD family, in contrast, uniformly showed the homozygous wild-type pattern.

DISCUSSION

The present studies provide the characterization of a specific alteration of protein structure underlying the qualitative platelet disorder PT-vWD. The heightened responsiveness of the platelets of patients with PT-vWD is associated with a substitution of valine for glycine at residue 233 of the mature GP Ibα protein. This substitution was not detected in the 322 chromosomes represented by the 161 individuals studied in the normal population. Absence in the normal population, tight linkage with phenotypic expression of disease, and absence of any additional abnormality of GP Ibα in these patients provide strong support for the glycine-to-valine mutation underlying the functional abnormality of the vWF receptor in PT-vWD.

Previous studies utilizing proteolytic fragments of GP Ibα and a variety of monoclonal antibodies have provided strong suggestions that the actual vWF-binding domain of the GP Ib/IX complex is contained within the 45-kDa amino-terminal region of GP Ibα (15–18). Studies of ristocetin- and botrocetin-mediated interaction of vWF with reconstituted GP Ib/IX complexes have provided further support for this concept (28,29). Recent efforts to localize the vWF binding site more specifically within the 293 residues of the 45-kDa amino-terminal region of GP Ibα have employed a series of overlapping synthetic peptides (30). However, no single peptide was found that exerted inhibitory activity in competitive binding assays comparable to that exerted by the 45-kDa tryptic fragment itself or by the larger proteolytic fragment of GP Ibα, glycocalicin.

A report by Handin and Petersen (31) on the expression of GP Ibα in vitro provided further information concerning the vWF binding site. COS cells transfected with a cDNA coding for the amino-terminal region but terminating before the beginning of the serine/threonine-rich domain at residue 320 produced recombinant protein capable of inhibiting ristocetin-induced binding of $^{125}$I-vWF to washed platelets. In contrast, a smaller recombinant product lacking nearly 100 additional amino acids at the carboxyl end (i.e., extending from the amino-terminal end through residue 220) lacked functional activity in this assay. The region extending from residue 220 to 320 of the mature GP Ibα accordingly appears to be critical for vWF binding. The glycine-to-valine mutation at residue 233 in the PT-vWD patients is thus well situated to produce an abnormality in vWF binding.

Substitution of a valine for a glycine may be anticipated to exert significant influence on the conformation of the resulting protein. For example, this precise amino acid substitution underlies the ras protooncogene-to-oncogene transformation where resulting conformational changes are believed to have profound functional sequelae (34,35). Computerized conformational energy analysis of GP polypeptides has indeed shown that a glycine-to-valine mutation at residue 233 produces major changes in conformation of this region of the protein. Since this substitution is associated with an abnormally enhanced interaction of patient platelets with native vWF under a variety of conditions (1–3) as well as with the unique ability of asialo-vWF to bind to formalin-fixed patient platelets or to agglutinate fresh patient platelets in the presence of EDTA (6), further study of the structural consequences of this mutation may lead to increased understanding of the mechanisms involving vWF-platelet interactions.

Several other families with PT-vWD (or pseudo-vWD) have been reported (2,3,36). Although the affected individuals share many aspects of phenotypic expression, it is quite possible that the underlying genetic abnormalities are not identical. Analysis of GP Ibα in the region of residues 220–320, and in particular at the 233 locus, may be an appropriate starting point for genetic analysis in such patients. Indeed, while at the time of the discovery of the ras mutation in human bladder carcinoma the only substitution in codon 12 of this gene demonstrated to cause malignant transformation of cultured fibroblasts was a glycine-to-valine mutation (32,33), subsequent investigations revealed that of the 19 possible amino acid substitutions for glycine at this position, all were in fact oncogenic, with the sole exception of proline (37).

We have shown that heterozygosity in the patient genome for the glycine-to-valine substitution is also reflected in the expression of both of the corresponding mRNAs in the patient platelets. It remains unknown, however, whether the resulting abnormal form of GP Ibα might have a selective advantage over the wild-type form in achieving membrane insertion and formation of the GP Ib/IX vWF receptor complex. Since there are no patients known to be homozygous for PT-vWD alleles, it has not been possible to study the effects of gene dosage on the function of this receptor. Through the application of in vitro expression in tissue culture cells, however, in which mutant vWF receptor molecules may be precisely engineered, it may soon prove possible to reach a fuller understanding of the structure-function properties of the platelet vWF receptor that result in clinical bleeding disorders.

CONFORMATIONAL ENERGY ANALYSIS

We determined the low energy conformations for GP Ibα peptides 228–238, containing five residues on amino and carboxyl ends of the central residue 233 for the peptide with Gly and with Val at this position. The sequence of this peptide is Tyr-Val-Trp-Lys-Gln-Gly (or Val)-Val-Asp-Val-Lys-Ala (SEQUENCE ID NO: 9 [Gly] and SEQUENCE ID NO: 10 [Val]). We now show that the substitution of Val for Gly 233 involves a local change in the conformation of this sequence that may be associated with the observed change in function of the vWF receptor.

METHODS

The low energy conformations for the peptide 228–238 in GP Ibα were determined using the chain build-up procedure (52). In this procedure all combinations of the single residue minima (46) for the first two amino acid residues (Tyr-Val) in the sequence were generated, and the resulting structures were subjected to energy minimization (53). All energy calculations were performed using the program ECEPP (Empirical Conformational Energies of Peptides Program (41,43)). The ground state or conformational energy of a given molecule, in particular of a polypeptide, can be computed manually according to the formula $$E_{TOT} = \sum_{i \neq j} \frac{Q_i Q_{ij}}{D r_{ij}} + \sum_{i \neq j} \epsilon_{ij} \left[ \left( \frac{R_{ij}}{r_{ij}} \right)^{12} - 2 \left( \frac{R_{ij}}{r_{ij}} \right)^{M} \right] + \sum_{k} A_k (1 \pm \cos(n\theta_k))$$

wherein $E_{TOT}$ is the total conformational energy of the peptide; the first summation is the total coulombic electrostatic interaction energy between all interacting atoms i and j in the molecule; the second is the total Lennard-Jones interaction potential; and the third is the total torsional energy of the molecule. $Q_i$ is the charge on the ith atom; D is the dielectric constant of the medium taken as 2; $r_{ij}$ is the distance between the ith and the jth atoms; $\epsilon_{ij}$ is the potential well depth at the minimum in the Lennard-Jones potential function; $R_{ij}$ is the distance between two atoms where the energy between them is a minimum; the exponent M is 6 for nonhydrogen-bonding atoms and 10 for hydrogen-bonding atoms; $A_K$ is the rotational barrier height for rotation around the kth bond; and n is 2 or 3 depending upon whether the bond is a single bond (cos $3\theta_K$) or a double bond (—cos $2\theta_K$); and $\theta_K$ is the kth dihedral angle. After energy minimization, all conformations whose energies lay within 5 kcal/mol of the energy of the global minimum (lowest energy structure) were retained. All combinations of conformations of these minima were taken with the single residue minima for the next amino acid residue (Trp) in the sequence. The above procedure was then repeated. The entire process was repeated until all amino acids in the sequence were 'added'. At all stages in the chain build-up procedure the amino terminus was blocked with the N-acetyl group while the carboxyl terminus was blocked with the $NH\text{-}CH_3$ group to simulate the effect of nearest-neighbor amino acids in the polypeptide chain (41).

The energy minima for the two GP Ibα peptides Tyr 228-Ala 238 were generated in the above-described manner. The minima for Tyr-Val-Trp-Lys-Gln were used for both sequences. The minima for the pentapeptide were then combined with the single residue minima for Gly or Val, and the remaining amino acids in each sequence were 'added' to each peptide (Gly- or Val-containing) using the above-described procedure. In all, approximately 5000 possible structures were generated for each peptide. All final conformations for both peptides were displayed on a Silicon Graphics Personal Iris Model 4D25G computer using the program Insight II (Biosym Corp., San Diego, Calif.).

It should be noted that the effects of solvation (54,55) were not expressly included in these calculations. At least half of the residues in each peptide are non-polar. It is thus possible that this region of the protein is shielded from the solvent. One subject of the calculations was therefore to determine whether the undecapeptide contained strong structural preferences in the absence of solvent. As presented in the Results section below, both wild-type and mutant peptides were found to adopt few low energy conformations, all of which would be expected to be stabilized by hydration.

RESULTS

The low energy minima found for the pentapeptide Tyr 228-Gln 232 are shown in Table II. In this table the conformations are given in terms of a single letter code defined in Zimmerman et al. (45). It may be seen that at the pentapeptide level a helical structure (residues in the A state) is favored. A number of other structures are predicted to exist for this peptide. After addition of Lys 236, few low energy structures remained. This pattern persisted through the addition of Ala 238 in the sequence. The results obtained for both undecapeptides are shown in Tables III and IV for Gly 233- and Val 233-containing peptides, respectively. These minima are prototypical for each peptide for all conformations whose energies lay within 5 kcal/mol of the global minimum. The only other minimum obtained for the Gly 233-containing peptide was a helical conformation disrupted at Val 236 (A* conformation). The statistical weight (41,45) of this conformation (whose energy relative to that of the global minimum was 3.1 kcal/mol) was <1%. Likewise, the only other minimum obtained from the substituted peptide (Val for Gly 233) was one in which Lys 237 adopted an A* conformation that disrupted a helix from Tyr 228-Val 236. The statistical weight of this conformer (relative energy of 2 kcal/mol) was likewise <1%. Thus the conformations listed in Tables III and IV are the most likely ones for the two peptides.

For the Gly 233-containing peptide (SEQUENCE ID

TABLE II

Computed Lowest Energy Structures for the Initial Pentapeptide N-Acetyl-Tyr—Val—Trp—Lys—Gln—$NHCH_3$, Residues 228–232, in Platelet GP Ibα

| | Conformational states[a] | | | | | Energy[b] |
|---|---|---|---|---|---|---|
| Conformer | Tyr | Val | Trp | Lys | Gln | (kcal/mol) |
| 1 | A | A | A | A | A | 0.0 |
| 2 | E | A | A | A | A | 1.2 |
| 3 | C | D | E | A* | E | 2.7 |
| 4 | A | A | A | A | C | 2.7 |
| 5 | A | A | A | C | F | 2.7 |
| 6 | E | A | A | A | C | 3.2 |

[a]These letter codes represent regions of conformational space. For example, A is α-helix, E is extended. A complete elaboration of the specific range of dihedral angles associated with each letter is given in Ref. 45.
[b]All conformational energies are given relative to the energy of the global minimum (lowest energy structure), conformer 1.

TABLE III

Computed Lowest Energy Structures for the Undecapeptide from Wild-Type GP Ibα, Residues 228–238, N-Acetyl-Tyr—Val—Trp—Lys—Gln—Gly—Val—Asp—Val—Lys—Ala—$NHCH_3$

| | Conformational states[a] | | | | | | | | | | | Energy[b] |
|---|---|---|---|---|---|---|---|---|---|---|---|---|
| Conformer | Tyr | Val | Trp | Lys | Gln | Gly | Val | Asp | Val | Lys | Ala | (kcal/mol) |
| 1 | A | A | A | A | C | D* | A | A | A | A | A | 0.0 |
| 2 | A | A | A | A | A | A | A | A | A | A | A | 2.1 |

[a]These letter codes represent regions of conformational space. For example, A is α-helix, E is extended. A complete elaboration of the specific range of dihedral angles associated with each letter is given in Ref. 45.
[b]All conformational energies are given relative to the energy of the global minimum (lowest energy structure), conformer 1.

TABLE IV

Computed Lowest Energy Structures for the Undecapeptide from PT-vWD GP Ibα, Residues 228–238, N-Acetyl-Tyr—Val—Trp—Lys—Gln—Val—Val—Asp—Val—Lys—Ala—$NHCH_3$

| | Conformational states[a] | | | | | | | | | | | Energy[b] |
|---|---|---|---|---|---|---|---|---|---|---|---|---|
| Conformer | Tyr | Val | Trp | Lys | Gln | Val | Val | Asp | Val | Lys | Ala | (kcal/mol) |
| 1 | A | A | A | A | A | A | A | A | A | A | A | 0.0 |
| 2 | B | A | A | A | A | A | A | A | A | A | A | 0.5 |

[a]These letter codes represent regions of conformational space. For example, A is α-helix, E is extended. A complete elaboration of the specific range of dihedral angles associated with each letter is given in Ref. 45.
[b]All conformational energies are given relative to the energy of the global minimum (lowest energy structure), conformer 1.

NO: 9), two types of structures resulted. The lowest energy structure (Table III) is helical, but the helix is disrupted at Gln 232-Gly 233 due to the formation of a chain reversal or bend conformation (CD* for conformer 1 in Table III). The D* conformation is a low energy conformation only for Gly and is forbidden for all L-α-amino acids (39). The other low energy structure for the Gly 233-containing peptide (SEQUENCE ID NO: 9), conformer 2 in Table III, is seen to be all-helical.

As shown in Table IV, for the Val 233-containing peptide (SEQUENCE ID NO: 10), two structures were also obtained. The lowest energy structure (conformer 1) was all helical. This structure is the same as the higher energy alternative one for the Gly 233-containing peptide (SEQUENCE ID NO: 9) (conformer 2, Table III). The other conformer for the Val 233-containing peptide (SEQUENCE ID NO: 10) is also helical except that Tyr 228 adopted a β conformation (conformer 2, Table IV) which probably represents an end effect (41,50). The structures of the lowest energy conformations for the Gly 233- and Val-233 containing peptides (SEQUENCE ID NO: 9 and SEQUENCE ID NO: 10, respectively) deviate from one another at positions 232 and 233 due to the disruption of the helical structure by the CD* bend conformation at Gln 232-Gly 233. The finding that only two low energy conformers exist for both peptides, from the thousands of possible structures generated for these peptides, suggests that the peptide Tyr 228-Ala 238 is highly structured in the protein. Similar results have been obtained for peptide segments in other proteins such as Val 5-Gly 12 of melittin (50) and Ile 55-Met 67 in the p21 protein (54).

The lowest energy conformers for the Gly and Val 233-containing peptides (SEQUENCE ID NO: 9 and SEQUENCE ID NO: 10, respectively) (conformers 1 in Tables III and IV) also deviate in hydrophobic regions and hydrophilic regions. The lowest energy conformation for the Val 233-containing peptides (SEQUENCE ID NO: 10) has a discrete hydrophobic surface composed of the side chains of Val 229, Val 233 and Val 236, Tyr 228 and the —$CH_2$ groups of Gln 232 while the side chains of Lys 231 and Asp 235 constitute a hydrophilic region opposite the hydrophobic region. Thus the helical structure for the Val 233-containing peptide (SEQUENCE ID NO: 10) is amphipathic. One important contributing residue to the hydrophobic face of this structure is Val 233. No such surface exists for the structure of the lowest energy conformer for the Gly 233-containing peptide (SEQUENCE ID NO: 9) (conformer 1 in Table III). On the other hand, the alternate structure for this peptide, which is all-helical (conformer 2 in Table III) is also an amphipathic structure but lacks the hydrophobic residue at position 233.

Both structures contain polar side chains that are 'exposed', i.e., that point away from the backbone. In the amphipathic structure the non-polar and polar side chains segregate. Both types of structures allow for maximal contact of polar residues with the solvent, i.e., water. Thus, despite the absence of inclusion of the effects of solvation in these calculations, both peptides tend to adopt structures that would be expected to allow good solvation of polar residues. It should be noted that previous calculations on the low energy conformations of peptides with polar residues, in which the effects of solvation are not included, resulted in structures that were in agreement with those observed experimentally and that allowed hydration of polar residues (39,41,42,55–58).

DISCUSSION

A major implication of these results is that the amphipathic surfaces in the 228–238 region of the Val 233-containing GP Ibα protein (SEQUENCE ID NO: 10) may associate strongly with complementary surfaces during vWF binding to the GPIb/IX receptor complex or may induce structural changes in the whole protein that result in heightened interaction with vWF. This stronger association might be altered in processes involving the normal receptor protein because the preferred conformation for the 228–238 region in non-amphipathic. Only if the Gly 233-peptide (SEQUENCE ID NO: 9) adopts the higher energy form would the hydrophobic surface exist. In this higher energy form, the normal protein would be active in promoting platelet aggregation.

The amphipathic structure found for the mutant form of GP Ibα that may promote platelet adhesion/aggregation suggests that particular changes in the sequence from Tyr 228-Ala 238 might significantly alter this association. For example, substitution of charged residues for non-polar ones might weaken, or even prevent, such association. Conversely, substitution of non-polar residues for polar ones may also diminish association. These might be tested in site-specific mutagenesis experiments and in studies with peptides from this region of the protein that compete with platelet GP Ibα for binding to vWF (30,38).

In addition, Gly 233 appears to be a critical residue because it promotes bend formation by adopting the unique D* conformation. If the D* conformation is critical at this position, then substitution of any L-amino acid residue (which cannot adopt the D* conformation) might be expected to result either in a non-functioning or an abnormally functioning protein. Certainly, non-polar helix-forming residues such as Leu, Met and-Phe, at position 233 would be expected to promote heightened interactions between vWF and the platelet GPIb/IX complex when substituted for Gly at this position and result in an abnormally functioning protein.

On the other hand, if simply bend formation at positions 232 and 233 is critical for regulation of ligand binding, then substitution for Gly 233 by strong helix-breaking and bend-forming residues such as Pro, should promote bend formation at positions 232 and 233, resulting in a complex that does not favor vWF binding. These predictions are potentially testable with the development of in vitro cell expression systems in which GP Ibα protein containing site-directed mutations at position 233 may be utilized in vWF binding studies.

Our computational results suggest a possible mechanism for the heightened platelet adhesion/aggregation seen in PT-vWD. In normal individuals, the lack of interaction between unstimulated platelets and vWF may be due to the low affinity of the lower energy, non-amphipathic conformation of the normal GP Ibα protein. Only by its interaction with activating agents can it be induced to adopt the less stable (active) conformation. In PT-vWD, the abnormal (Val 233-containing) GP Ibα protein (SEQUENCE ID NO: 10) may exist permanently in the activated conformation, one in which hydrophobic and hydrophilic residues form discrete clusters. These regions may either interact directly with vWF or may induce other structural changes in the protein. This structurally altered protein may then bind with high affinity to vWF.

The above conclusions are based on the computed strong structural preferences found for each 228–238 peptide from GP Ibα. The assumption was made that any long-range interactions that exist between the peptide segment and the remainder of the protein further stabilize the inferred structures and do not significantly change them. The findings that the peptides adopt only a limited number of conformations and that substitution of Val for Gly 233 causes a local conformational change that stabilizes an amphipathic conformation suggest that this peptide segment undergoes a change in structure that alters the functioning of the protein.

Expression of the Polypeptides

The recombinant baculovirus expression vector system was used for the production in insect cells of mutant polypeptides. Standard methods of site-directed mutagenesis were employed to create a codon coding for valine in place of the wild type glycine at codon 233 of the wild type human platelet GP Ibα cDNA. The success of the site-directed mutagenesis was confirmed by DNA sequencing of the resultant mutant cDNA. Following this, the mutant full length cDNA was subcloned into the baculovirus transfer vector pVL 1392. This was accomplished by symmetric cloning into the Eco RI cloning site of the transfer vector. Following this, correct orientation of resulting constructs was determined by restriction mapping. A correctly oriented cDNA (i.e. correctly oriented with respect to the baculovirus promoter) was then grown up into a large plasmid preparation. Following this, using the standard methods in the manual of Summers and Smith (reference cited above), the plasmid containing the mutant full length GP Ibα sequence was co-transfected with wild-type baculovirus (*Autographa californica* nuclear polyhedrosis virus: AcNPV) into SF9 insect cells. A series of five rounds of dot-blot hybridization was then employed, in which multiple successive dilutions of the transfected cells were probed with a complementary $DNA^-$ sequence representing genuine GP Ibα. By this process of limiting dilutions, a purified recombinant virus that did not produce the polyhedra associated with the wild type baculovirus, but did show strong hybridization to the GP Ibα probe, was isolated. This virus was then used to infect fresh SF9 or subsequently SF21 insect cells. Recombinant protein corresponding to the mutant GP Ibα protein was then harvested from the insect cells.

The expression of the wild-type GP Ibα protein in insect cells resulted in a major protein band migrating at 78–80 kD on SDS-PAGE. The band was electro-phoretically transferred to nitrocellulose and stained in Western blots by polyclonal antibodies directed against both the carboxyl-terminal cytoplasmic end of platelet GP Ibα (amino acids 582–600) and against the major extracellular portion of platelet GP Ibα (glycocalicin). The recombinant wild-type protein distributed into the insoluble fraction of NP-40 extracts of insect cell lysates, but was solubilized in the presence of 6M guanidine. Subsequent removal of the guanidine by dialysis resulted in a semipurified source of soluble recombinant protein which inhibited von Willebrand factor (vWF) dependent platelet agglutination in a dose-dependent manner, with an $IC_{50}$ of approximately 1 μM. The recombinant protein was thus positively identified as GP Ibα, wild type. The length of the expressed protein is expectedly shorter than the naturally-occurring protein due to the expression within an insect cell. An insect cell expresses DNA encoding sugars different from a mammalian cell, and proteins expressed in such insect cells characteristically migrate faster on SDS-PAGE than their naturally-occurring mammalian counterparts.

Similar procedures, such as SDS PAGE, were also used to confirm the identity of the mutant polypeptide expressed by the insect cells. The insect cells infected with virus containing cDNA encoding the mutant polypeptide also expressed protein which showed a major band migrating at 78–80 kD on SDS-PAGE.

Although certain preferred embodiments have been depicted and described in detail herein, it will be apparent to those skilled in the relevant art that various modifications, additions, substitutions and the like can be made without departing from the spirit of the invention, and these are therefor considered to be within the scope of the invention as defined by the appended claims.

REFERENCES

1. Miller, J. L. and Castella, A., Blood 60: 790–794 (1982).
2. Weiss, H. J. et al., N. Engl. J. Med. 306: 326–362 (1982).
3. Takahashi, H., Thromb. Res. 19: 857–867 (1980).
4. Miller, J. L. et al., J. Clin. Invest. 7.2: 1532–1542 (1983).
5. Takahaski, H. et al., Blood 64: 1254–1262 (1984).
6. Miller, J. L. et al., Blood 70: 1804–1809 (1987).
7. Miller, J. L. et al., Br. J. Haematol. 74: 313–319 (1990).
8. George, J. N. et al, N Engl J Med 311: 1084–1098 (1984).
9. Du, X. et al., Blood 69: 1524–1527 (1987).
10. Fitzgerald, L. A. and Phillips, D. R., in Platelet Immunobiology: Molecular and Clinical Aspects, eds. Kunicki, T. J. and George, J. N. (Lippincott, Philadelphia), pp. 9–30 (1989).
11. Lopez, J. A. et al., Proc. Natl. Acad. Sci. USA 84: 5615–5619 (1987).
12. Wicki, A. N. et al., Thromb. Haemostasis 61: 448–453 (1989).
13. Wenget, R. H. et al., Biochem. Biophys. Res. Commun. 156: 389–395 (1988).
14. Petersen, E. et al. , Blood 72: 335a (abstr.) (1988).
15. Wicki, A. N. and Clemetson, K. J. , Eur. J. Biochem. 153: 1–11 (1985).
16. Brower, M. S. et al. , J. Clin. Invest. 75: 657–666 (1985).
17. Handa, M. et al., J. Biol. Chem. 261: 12579–12585 (1986).
18. Vicente, V. et al., J. Biol. Chem. 263: 18473–18479 (1988).
19. Bell, G. I. et al., Proc. Natl. Acad. Sci. USA 78: 5759–5763 (1981).
20. Sambrook, J. et al., Molecular Cloning: A Laboratory Manual (Cold Spring Harbor Lab., Cold Spring Harbor, N.Y.) (1989).
21. Kawasaki, E. S., in PCR Protocols, eds. Innis, M. et al., (Academic, San Diego) pp. 146–152 (1990).
22. Finch, C. N. et al., Blood 75: 2357–2362 (1990).
23. Sanger, F. et al., Proc. Natl. Acac. Sci. USA 74: 5463–5467 (1977).
24. Carothers, A. M. et al. , Biotechniques 7: 494–499 (1990).
75. Gibbs, R. A. et al. , Nucleic Acids Res. 17: 2437–2448 (1989).
26. Morton, N. E., Hum. Genet. 7: 277–318 (1955).
27. Lange, K. et al., Genet. Epidemiol. 5: 471–472 (1988).
28. Berndt, M. C. et al., Biochemistry 27: 633–640 (1988).
29. Andrews, R. K. et al. , Biochemistry 28: 8317–8326 (1989).
30. Vicente, V. et al., J. Biol. Chem. 265: 274–280 (1990).
31. Handin, R. I. and Petersen, E. , Blood 74: 129a (abstr.) (1989).
32. Reddy, E. P. et al., Nature (London) 300: 149–152 (1982).
33. Tabin, C. J. et al., Nature (London) 300: 143–148 (1982).
34. Varmus, in The Molecular Basis of Blood Diseases, eds. Stamatoyannopoulos, G. et al., (Saunders, Philadelphia), pp. 271–346 (1987).
35. Pincus, M. R. and Brandt-Rauf, P. W., Cancer Invest. 185–195 (1985).
36. Bryckaert, M. C. et al., J. Lab. Clin. Med. 106: 393–400 (1985).
37. Seeburg, P. H. et al. , Nature (London) 312: 71–75 (1984).
38. Katagari, Y. et al. , Thromb. Haemost. 63: 122–126 (1990).
39. Pincus, M. R. and Scheraga, H. A., Accnt. Chem. Res. 18: 372–379 (1985).
40. Chen, J. M. et al. , J. Biomol. Struct. Dynam. 6: 859–875 (1989).
41. Scheraga, H. A., Carlsberg Res. Commun. 49: 1–55 (1984).
42. Scheraga, H. A., in Biological and Artificial Intelligence Systems (Clementi, E. and Chin, S., eds.), pp. 1–14 (ESCOM Science Publishers) (1988).
43. Nemthy, G. et al. , J. Phys. Chem. 87: 1883–1887 (1983).
44. Anfinsen, C. B. and Scheraga, H. A. , Adv. Protein Chem. 29: 205–300 (1975).
45. Zimmerman, S. S. et al. , Macromolecules 10: 1–9 (1977).
46. vasquez, M. et al., Macromolecules 16: 1043–1049 (1983).
47. Paine, G. H. and Scheraga, H. A., Biopolymers 24: 1391–1436 (1985).
48. Miller, M. H. and Scheraga, H. A. , J. Polym. Sci. Polym. Syrup. 54: 171–200 (1976).
49. Dygert, M. et al. , Macromolecules 8: 750–761 (1975).
50. Pincus, M. R. et al., Proc. Natl. Acad. Sci. USA 79: 5107–5110 (1982).
51. Ponnuswamy, P. K. et al., Proc. Natl. Acad. Sci. USA 70: 830–833 (1973).
52. Pincus, M. R., Int. J. Quantum Chem. Quant. Biol. Symp. 15: 209–220 (1988).
53. Powell, M. J. D., Comput. J. 18: 155–162 (1964).
54. Pincus, M. R. et al., Proc. Natl. Acad. Sci. USA 84: 8375–8379 (1987).
55. Hodes, Z. I. et al., Biopolymers 18: 1565–1610 (1979).
56. Simon, I. et al., Macromolecules 11: 797–804 (1978).
57. Pincus, M. R. et al. , J. Protein Chern. 2: 131–140 (1983).
58. Pincus, M. R. et al., Proc. Natl. Acad. Sci. USA 84: 4821–4825 (1987).

What is claimed is:

1. An isolated polypeptide encoded by an amino acid sequence for wild-type platelet glycoprotein Ib alpha having a mutation other than at amino acid 233 and within the region 228–238 which renders said polypeptide more reactive with von Willebrand factor than wild-type platelet glycoprotein Ib alpha, as measured by a ristocetin assay, wherein said mutation alters the three dimensional structure of said polypeptide, such that the lowest energy conformation of the polypeptide changes from a beta bend conformation to an amphipathic alpha helix conformation within the region 232–233 of said polypeptide.

2. A composition comprising an amount of the polypeptide of claim 1 effective to inhibit platelet adhesion/aggregation and a compatible carrier.

3. A pharmaceutical composition comprising an amount of the polypeptide of claim 1 effective to inhibit platelet adhesion/aggregation and a pharmaceutically acceptable carrier.

4. A method of inhibiting platelet adhesion/aggregation which comprises contacting the platelets with an amount of the polypeptide of claim 1 effective to inhibit adhesion/aggregation of the platelets.

5. An isolated fragment of the polypeptide of claim 1, wherein said fragment includes the region 228–238 of said polypeptide.

6. A composition comprising an amount of the fragment of claim 5 effective to inhibit platelet adhesion/aggregation and a compatible carrier.

7. A pharmaceutical composition comprising an amount of the fragment of claim 5 effective to inhibit platelet adhesion/aggregation and a pharmaceutically acceptable carrier.

8. A method of inhibiting platelet adhesion/aggregation which comprises contacting the platelets with an amount of the fragment of claim 5 effective to inhibit adhesion/aggregation of the platelets.

9. An isolated polypeptide encoded by an amino acid sequence for wild-type platelet glycoprotein Ib alpha having a mutation which substitutes an amino acid for glycine at amino acid 233.

10. The polypeptide of claim 9 wherein the amino acid substituted for glycine comprises valine.

11. A composition comprising an amount of the polypeptide of claim 9 effective to inhibit platelet adhesion/aggregation and a compatible carrier.

12. A pharmaceutical composition comprising an amount of the polypeptide of claim 9 effective to inhibit platelet adhesion/aggregation and a pharmaceutically acceptable carrier.

13. A method of inhibiting platelet adhesion/aggregation which comprises contacting the platelets with an amount of the polypeptide of claim 9 effective to inhibit adhesion/aggregation of the platelets.

14. An isolated fragment of the polypeptide of claim 9, wherein said fragment includes the region 228–238 of said polypeptide.

15. A composition comprising an amount of the fragment of claim 14 effective to inhibit platelet adhesion/aggregation and a compatible carrier.

16. A pharmaceutical composition comprising an amount of the fragment of claim 14 effective to inhibit platelet adhesion/aggregation and a pharmaceutically acceptable carrier.

17. A method of inhibiting platelet adhesion/aggregation which comprises contacting the platelets with an amount of the fragment of claim 14 effective to inhibit adhesion/aggregation of the platelets.

* * * * *